(12) United States Patent
Maclennan et al.

(10) Patent No.: US 7,074,560 B2
(45) Date of Patent: Jul. 11, 2006

(54) PURIFICATION OF TISSUE PLASMINOGEN ACTIVATOR (TPA)

(75) Inventors: John Moore Maclennan, Bellingham, MA (US); Robert Charles Ladner, Ijamsville, MD (US); Thomas Cushman Ransohoff, Lexington, MA (US)

(73) Assignee: Dyax Corp., Cambridge, MA (US)

( * ) Notice: Subject to any disclaimer, the term of this patent is extended or adjusted under 35 U.S.C. 154(b) by 337 days.

(21) Appl. No.: 10/193,588

(22) Filed: Jul. 11, 2002

(65) Prior Publication Data

US 2003/0162942 A1    Aug. 28, 2003

Related U.S. Application Data

(60) Division of application No. 09/497,435, filed on Feb. 3, 2000, now Pat. No. 6,462,172, which is a division of application No. 08/821,744, filed on Mar. 20, 1997, now Pat. No. 6,084,062, which is a continuation-in-part of application No. 08/619,885, filed on Mar. 20, 1996, now abandoned.

(51) Int. Cl.
| | |
|---|---|
| C07H 21/04 | (2006.01) |
| A61K 38/00 | (2006.01) |
| C07K 1/00 | (2006.01) |
| C11P 21/06 | (2006.01) |
| C12N 15/00 | (2006.01) |

(52) U.S. Cl. ............ 435/6; 435/5; 435/320.1; 435/69.1; 435/DIG. 37; 536/23.2; 536/23.4; 536/23.5

(58) Field of Classification Search .......... 435/5, 435/6, 320.1, 69.1, 69.7, DIG. 1, DIG. 37; 536/23.1, 23.2, 23.4, 23.5

See application file for complete search history.

(56) References Cited

U.S. PATENT DOCUMENTS

| | | | |
|---|---|---|---|
| 4,708,944 | A | 11/1987 | Someno et al. |
| 4,898,825 | A | 2/1990 | Morii et al. |
| 5,133,866 | A | 7/1992 | Kauvar |
| 5,141,862 | A | 8/1992 | Patel et al. |
| 5,223,409 | A | 6/1993 | Ladner et al. |
| 5,227,297 | A | 7/1993 | Patel et al. |
| 5,403,484 | A | 4/1995 | Ladner et al. |
| 6,084,062 | A * | 7/2000 | Maclennan et al. ......... 530/324 |

FOREIGN PATENT DOCUMENTS

EP    0 112 122 A2    6/1984

OTHER PUBLICATIONS

Bode et al., *The refined 2.0 angstrom X-ray crystal structure of the complex formed between bovine beta-trypsin and CMTI-I, a trypsin inhibitor from squash seeds (Cucurbita maxima)*. Febs Letters 242 (2):285-292.
Boschetti, *Advanced sorbents for preparative protein separation purposes*, J. Chromatography A, 658: 207-236 (1994).
Garrard & Henner, Gene 128: 103-109 (1993).
Huang et al., *Affinity purification of von Willebrand factor using ligands derived from peptide libraries*, Bioorganic & Medicinal Chem., 4(5): 699-708 (1996).
Knight, *Bioseparations: media and modes*, Bio/Technology, 8: 200-201 (1990).
Ladner, *Constrained peptides as binding entities*, Trends in Biotechnology, 13(10): 426-430 (1995).
Le Nguyen et al, *Solid phase synthesis of a trypsin inhibitor isolated from the Cucurbitaceae Ecballium elaterium*, Int. J. Peptide Protein Res., 34: 492-497 (1989).
Markland et al., *Selection for protease inhibitors using bacteriophage display*, Methods Enzymol., 267: 28-51 (1996).
Narayanan, *Preparative affinity chromatography of proteins*, J. Chromatography A, 658: 237-258 (1994).
Scopes, *Protein Purification: Principles and Practice*, New York, Springer-Verlag, 111-112, 117-125 (1982).
Vedvick et al., *High-level secretion of biologically active aprotinin from the yeast Pichia pastoris*, J. Industrial Microbiol., 7: 197-202 (1991).
Wagner et al., *High level expression, purification, and characterization of the Kunitz-type protease inhibitor domain of protease nexin-2/amyloid β-protein precursor*, Biochem. Biophys Res. Comm., 186(2): 1138-1145 (1992).
Weiczorek et al., *The squash family of serine proteinase inhibitors*, BBRC, 126:646-652 (1985).
Kupryszewski et al., "Synthesis of Trypsin Inhibitor CMTI I from Squash Seeds," Polish J. of Chem., 1987, vol. 61, pp. 789-793.
PCT International Search Report, mailed Jul. 8, 1998.

* cited by examiner

*Primary Examiner*—Padmashri Ponnaluri
(74) *Attorney, Agent, or Firm*—Fish & Richardson P.C.

(57) ABSTRACT

A method is disclosed for obtaining affinity ligands for isolating tissue-type plasminogen activator (tPA). Ligands binding tPA with high specificity at pH 7 and releasing tPA at pH 5 or lower are disclosed. Also disclosed are methods whereby additional ligands having desirable preselected binding and release (elution) characteristics may be isolated, permitting the development of tailored ligands to meet the purification problems presented by any particular feed stream containing tPA.

25 Claims, 4 Drawing Sheets

SEQUENCE LISTING

```
<160> NUMBER OF SEQ ID NOS: 43

<210> SEQ ID NO 1
<211> LENGTH: 29
<212> TYPE: PRT
<213> ORGANISM: Cucurbita maxima

<400> SEQUENCE: 1

Arg Val Cys Pro Arg Ile Leu Met Glu Cys Lys Lys Asp Ser Asp Cys
1               5                   10                  15

Leu Ala Glu Cys Val Cys Leu Glu His Gly Tyr Cys Gly
            20                  25

<210> SEQ ID NO 2
<211> LENGTH: 50
<212> TYPE: PRT
<213> ORGANISM: Artificial Sequence
<220> FEATURE:
<223> OTHER INFORMATION: CMTI-I Library design
<220> FEATURE:
<221> NAME/KEY: MISC_FEATURE
<222> LOCATION: (7)..(7)
<223> OTHER INFORMATION: X = L,S,W,P,Q,R,M,T,K,V,A,E or G
<220> FEATURE:
<221> NAME/KEY: MISC_FEATURE
<222> LOCATION: (9)..(9)
<223> OTHER INFORMATION: X = F,S,Y,C,L,P,H,R,I,T,N,V,A,D or G
<220> FEATURE:
<221> NAME/KEY: MISC_FEATURE
<222> LOCATION: (10)..(10)
<223> OTHER INFORMATION: X = K,R,T or I
<220> FEATURE:
<221> NAME/KEY: MISC_FEATURE
<222> LOCATION: (11)..(12)
<223> OTHER INFORMATION: X = F,S,Y,C,L,P,H,R,I,T,N,V,A,D or G
<220> FEATURE:
<221> NAME/KEY: MISC_FEATURE
<222> LOCATION: (13)..(13)
<223> OTHER INFORMATION: X = L,S,W,P,Q,R,M,T,K,V,A,E or G
<220> FEATURE:
<221> NAME/KEY: MISC_FEATURE
<222> LOCATION: (14)..(14)
```

-continued

<223> OTHER INFORMATION: X = E,K,R or G

<400> SEQUENCE: 2

Phe Tyr Ser Gly Ala Arg Xaa Cys Xaa Xaa Xaa Xaa Xaa Cys Lys
1               5                  10                  15

Lys Asp Ser Asp Cys Leu Ala Glu Cys Val Cys Leu Glu His Gly Tyr
            20                  25                  30

Cys Gly Ala Gly Pro Ser Tyr Ile Glu Gly Arg Ile Val Gly Ser Ala
        35                  40                  45

Ala Glu
    50

<210> SEQ ID NO 3
<211> LENGTH: 150
<212> TYPE: DNA
<213> ORGANISM: Artificial Sequence
<220> FEATURE:
<223> OTHER INFORMATION: coding sequence for CMTI-I Library
<220> FEATURE:
<221> NAME/KEY: misc_feature
<222> LOCATION: (19)..(20)
<223> OTHER INFORMATION: n= a,c,g or t
<220> FEATURE:
<221> NAME/KEY: misc_feature
<222> LOCATION: (25)..(26)
<223> OTHER INFORMATION: n= a,c,g or t
<220> FEATURE:
<221> NAME/KEY: misc_feature
<222> LOCATION: (29)..(29)
<223> OTHER INFORMATION: n= a,c,g or t
<220> FEATURE:
<221> NAME/KEY: misc_feature
<222> LOCATION: (31)..(32)
<223> OTHER INFORMATION: n= a,c,g or t
<220> FEATURE:
<221> NAME/KEY: misc_feature
<222> LOCATION: (34)..(35)
<223> OTHER INFORMATION: n= a,c,g or t
<220> FEATURE:
<221> NAME/KEY: misc_feature
<222> LOCATION: (37)..(38)
<223> OTHER INFORMATION: n= a,c,g or t

<400> SEQUENCE: 3
ttctattccg gagcccgtnn gtgtnntana nntnntnngr rgtgtaagaa ggattctgat        60
tgcttagcag aatgcgtttg cctcgagcat ggttattgtg gcgccggtcc ttcatacatt       120
gaaggtcgta ttgtcggtag cgccgctgaa                                        150

<210> SEQ ID NO 4
<211> LENGTH: 29
<212> TYPE: PRT
<213> ORGANISM: Artificial Sequence
<220> FEATURE:
<223> OTHER INFORMATION: tPA binding peptide

<400> SEQUENCE: 4

Arg Trp Cys Pro Lys Thr Ser Leu Gly Cys Met Lys Asp Ser Asp Cys
1               5                  10                  15

Leu Ala Glu Cys Val Cys Leu Glu His Gly Tyr Cys Gly
            20                  25

<210> SEQ ID NO 5
<211> LENGTH: 29
<212> TYPE: PRT
<213> ORGANISM: Artificial Sequence
<220> FEATURE:
<223> OTHER INFORMATION: tPA binding peptide

```
<400> SEQUENCE: 5

Arg Leu Cys Pro Lys Thr Tyr Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 6
<211> LENGTH: 29
<212> TYPE: PRT
<213> ORGANISM: Artificial Sequence
<220> FEATURE:
<223> OTHER INFORMATION: tPA binding peptide

<400> SEQUENCE: 6

Arg Trp Cys Ser Thr Tyr Ser Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 7
<211> LENGTH: 29
<212> TYPE: PRT
<213> ORGANISM: Artificial Sequence
<220> FEATURE:
<223> OTHER INFORMATION: tPA binding peptide

<400> SEQUENCE: 7

Arg Trp Cys Ser Thr Tyr Ser Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 8
<211> LENGTH: 29
<212> TYPE: PRT
<213> ORGANISM: Artificial Sequence
<220> FEATURE:
<223> OTHER INFORMATION: tPA binding peptide

<400> SEQUENCE: 8

Arg Leu Cys Pro Lys Thr Ser Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 9
<211> LENGTH: 29
<212> TYPE: PRT
<213> ORGANISM: Artificial Sequence
<220> FEATURE:
<223> OTHER INFORMATION: tPA binding peptide

<400> SEQUENCE: 9

Arg Trp Cys Ser Thr Tyr Ser Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 10
<211> LENGTH: 29
<212> TYPE: PRT
<213> ORGANISM: Artificial Sequence
<220> FEATURE:
```

<223> OTHER INFORMATION: tPA binding peptide

<400> SEQUENCE: 10

Arg Leu Cys Pro Lys Thr Ser Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 11
<211> LENGTH: 29
<212> TYPE: PRT
<213> ORGANISM: Artificial Sequence
<220> FEATURE:
<223> OTHER INFORMATION: tPA binding peptide

<400> SEQUENCE: 11

Arg Trp Cys Ser Lys Ser Ser Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 12
<211> LENGTH: 29
<212> TYPE: PRT
<213> ORGANISM: Artificial Sequence
<220> FEATURE:
<223> OTHER INFORMATION: tPA binding peptide

<400> SEQUENCE: 12

Arg Leu Cys Pro Lys Thr Asp Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 13
<211> LENGTH: 29
<212> TYPE: PRT
<213> ORGANISM: Artificial Sequence
<220> FEATURE:
<223> OTHER INFORMATION: tPA binding peptide

<400> SEQUENCE: 13

Arg Trp Cys Pro Lys Ser Ser Met Gly Cys Lys Lys Asp Ser Asp Cys
1               5                   10                  15

Leu Ala Glu Cys Val Cys Leu Glu His Gly Tyr Cys Gly
            20                  25

<210> SEQ ID NO 14
<211> LENGTH: 29
<212> TYPE: PRT
<213> ORGANISM: Artificial Sequence
<220> FEATURE:
<223> OTHER INFORMATION: tPA binding peptide

<400> SEQUENCE: 14

Arg Trp Cys Pro Arg Thr Val Gln Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 15
<211> LENGTH: 29
<212> TYPE: PRT
<213> ORGANISM: Artificial Sequence

```
<220> FEATURE:
<223> OTHER INFORMATION: tPA binding peptide

<400> SEQUENCE: 15

Arg Trp Cys Pro Thr Ala Pro Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 16
<211> LENGTH: 29
<212> TYPE: PRT
<213> ORGANISM: Artificial Sequence
<220> FEATURE:
<223> OTHER INFORMATION: tPA binding peptide

<400> SEQUENCE: 16

Arg Leu Cys Pro Lys Thr Asp Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 17
<211> LENGTH: 29
<212> TYPE: PRT
<213> ORGANISM: Artificial Sequence
<220> FEATURE:
<223> OTHER INFORMATION: tPA binding peptide

<400> SEQUENCE: 17

Arg Trp Cys Pro Lys Ser Ala Leu Asp Cys Lys Lys Asp Ser Asp Cys
1               5                   10                  15

Leu Ala Glu Cys Val Cys Leu Glu His Gly Tyr Cys Gly
            20                  25

<210> SEQ ID NO 18
<211> LENGTH: 29
<212> TYPE: PRT
<213> ORGANISM: Artificial Sequence
<220> FEATURE:
<223> OTHER INFORMATION: tPA binding peptide

<400> SEQUENCE: 18

Arg Trp Cys Thr Lys Thr Ser Arg Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 19
<211> LENGTH: 29
<212> TYPE: PRT
<213> ORGANISM: Artificial Sequence
<220> FEATURE:
<223> OTHER INFORMATION: tPA binding peptide

<400> SEQUENCE: 19

Arg Trp Cys Ile Arg Thr Asp Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 20
<211> LENGTH: 29
<212> TYPE: PRT
```

```
<213> ORGANISM: Artificial Sequence
<220> FEATURE:
<223> OTHER INFORMATION: tPA binding peptide

<400> SEQUENCE: 20

Arg Trp Cys Pro Lys Thr Ser Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 21
<211> LENGTH: 29
<212> TYPE: PRT
<213> ORGANISM: Artificial Sequence
<220> FEATURE:
<223> OTHER INFORMATION: tPA binding peptide

<400> SEQUENCE: 21

Arg Trp Cys Pro Arg Thr Val Arg Arg Cys Met Lys Asp Ser Asp Cys
1               5                   10                  15

Leu Ala Glu Cys Val Cys Leu Glu His Gly Tyr Cys Gly
            20                  25

<210> SEQ ID NO 22
<211> LENGTH: 29
<212> TYPE: PRT
<213> ORGANISM: Artificial Sequence
<220> FEATURE:
<223> OTHER INFORMATION: tPA binding peptide

<400> SEQUENCE: 22

Arg Trp Cys Pro Lys Thr His Lys Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 23
<211> LENGTH: 29
<212> TYPE: PRT
<213> ORGANISM: Artificial Sequence
<220> FEATURE:
<223> OTHER INFORMATION: tPA binding peptide

<400> SEQUENCE: 23

Arg Trp Cys Pro Lys Thr Ser Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 24
<211> LENGTH: 29
<212> TYPE: PRT
<213> ORGANISM: Artificial Sequence
<220> FEATURE:
<223> OTHER INFORMATION: tPA binding peptide

<400> SEQUENCE: 24

Arg Trp Cys Pro Lys Ser Thr Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 25
<211> LENGTH: 29
```

```
<212> TYPE: PRT
<213> ORGANISM: Artificial Sequence
<220> FEATURE:
<223> OTHER INFORMATION: tPA binding peptide

<400> SEQUENCE: 25

Arg Trp Cys Pro Lys Ser Thr Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 26
<211> LENGTH: 29
<212> TYPE: PRT
<213> ORGANISM: Artificial Sequence
<220> FEATURE:
<223> OTHER INFORMATION: tPA binding peptide

<400> SEQUENCE: 26

Arg Trp Cys Pro Lys Tyr Thr Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 27
<211> LENGTH: 29
<212> TYPE: PRT
<213> ORGANISM: Artificial Sequence
<220> FEATURE:
<223> OTHER INFORMATION: tPA binding peptide

<400> SEQUENCE: 27

Arg Trp Cys Pro Arg Ser Ser Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 28
<211> LENGTH: 29
<212> TYPE: PRT
<213> ORGANISM: Artificial Sequence
<220> FEATURE:
<223> OTHER INFORMATION: tPA binding peptide

<400> SEQUENCE: 28

Arg Trp Cys Pro Lys Tyr Thr Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 29
<211> LENGTH: 29
<212> TYPE: PRT
<213> ORGANISM: Artificial Sequence
<220> FEATURE:
<223> OTHER INFORMATION: tPA binding peptide

<400> SEQUENCE: 29

Arg Trp Cys Pro Arg Ser Asn Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 30
```

```
<211> LENGTH: 29
<212> TYPE: PRT
<213> ORGANISM: Artificial Sequence
<220> FEATURE:
<223> OTHER INFORMATION: tPA binding peptide

<400> SEQUENCE: 30

Arg Trp Cys Pro Arg Ser Asn Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 31
<211> LENGTH: 29
<212> TYPE: PRT
<213> ORGANISM: Artificial Sequence
<220> FEATURE:
<223> OTHER INFORMATION: tPA binding peptide

<400> SEQUENCE: 31

Arg Trp Cys Pro Lys Tyr Thr Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 32
<211> LENGTH: 29
<212> TYPE: PRT
<213> ORGANISM: Artificial Sequence
<220> FEATURE:
<223> OTHER INFORMATION: tPA binding peptide

<400> SEQUENCE: 32

Arg Trp Cys Pro Lys Tyr Thr Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 33
<211> LENGTH: 29
<212> TYPE: PRT
<213> ORGANISM: Artificial Sequence
<220> FEATURE:
<223> OTHER INFORMATION: tPA binding peptide

<400> SEQUENCE: 33

Arg Trp Cys Pro Lys Tyr Thr Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 34
<211> LENGTH: 29
<212> TYPE: PRT
<213> ORGANISM: Artificial Sequence
<220> FEATURE:
<223> OTHER INFORMATION: tPA binding peptide

<400> SEQUENCE: 34

Arg Trp Cys Pro Arg Ser Thr Leu Glu Cys Met Lys Asp Ser Asp Cys
1               5                   10                  15

Leu Ala Glu Cys Val Cys Leu Glu His Gly Tyr Cys Gly
            20                  25
```

```
<210> SEQ ID NO 35
<211> LENGTH: 29
<212> TYPE: PRT
<213> ORGANISM: Artificial Sequence
<220> FEATURE:
<223> OTHER INFORMATION: tPA binding peptide

<400> SEQUENCE: 35

Arg Trp Cys Pro Lys Thr Ser Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 36
<211> LENGTH: 29
<212> TYPE: PRT
<213> ORGANISM: Artificial Sequence
<220> FEATURE:
<223> OTHER INFORMATION: tPA binding peptide

<400> SEQUENCE: 36

Arg Trp Cys Pro Lys Tyr Thr Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 37
<211> LENGTH: 29
<212> TYPE: PRT
<213> ORGANISM: Artificial Sequence
<220> FEATURE:
<223> OTHER INFORMATION: tPA binding peptide

<400> SEQUENCE: 37

Arg Trp Cys Pro Arg Ser Ser Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 38
<211> LENGTH: 29
<212> TYPE: PRT
<213> ORGANISM: Artificial Sequence
<220> FEATURE:
<223> OTHER INFORMATION: tPA binding peptide

<400> SEQUENCE: 38

Arg Trp Cys Pro Lys Ser Thr Leu Gly Cys Met Lys Asp Ser Asp Cys
1               5                   10                  15

Leu Ala Glu Cys Val Cys Leu Glu His Gly Tyr Cys Gly
            20                  25

<210> SEQ ID NO 39
<211> LENGTH: 29
<212> TYPE: PRT
<213> ORGANISM: Artificial Sequence
<220> FEATURE:
<223> OTHER INFORMATION: tPA binding peptide

<400> SEQUENCE: 39

Arg Trp Cys Pro Arg Ser Ser Leu Glu Cys Met Lys Asp Ser Asp Cys
1               5                   10                  15

Leu Ala Glu Cys Val Cys Leu Glu His Gly Tyr Cys Gly
            20                  25
```

<210> SEQ ID NO 40
<211> LENGTH: 29
<212> TYPE: PRT
<213> ORGANISM: Artificial Sequence
<220> FEATURE:
<223> OTHER INFORMATION: tPA binding peptide

<400> SEQUENCE: 40

Arg Trp Cys Pro Arg Ser Asn Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 41
<211> LENGTH: 29
<212> TYPE: PRT
<213> ORGANISM: Artificial Sequence
<220> FEATURE:
<223> OTHER INFORMATION: tPA binding peptide

<400> SEQUENCE: 41

Arg Trp Cys Pro Arg Ser Asn Leu Glu Cys Met Lys Asp Ser Asp Cys
1               5                   10                  15

Leu Ala Glu Cys Val Cys Leu Glu His Gly Tyr Cys Gly
            20                  25

<210> SEQ ID NO 42
<211> LENGTH: 29
<212> TYPE: PRT
<213> ORGANISM: Artificial Sequence
<220> FEATURE:
<223> OTHER INFORMATION: tPA binding peptide
<220> FEATURE:
<221> NAME/KEY: MISC_FEATURE
<222> LOCATION: (2)..(2)
<223> OTHER INFORMATION: X = Trp or Leu
<220> FEATURE:
<221> NAME/KEY: MISC_FEATURE
<222> LOCATION: (4)..(4)
<223> OTHER INFORMATION: X = Pro, Ser, Thr or Ile
<220> FEATURE:
<221> NAME/KEY: MISC_FEATURE
<222> LOCATION: (5)..(5)
<223> OTHER INFORMATION: X = Arg, Lys or Thr
<220> FEATURE:
<221> NAME/KEY: MISC_FEATURE
<222> LOCATION: (6)..(6)
<223> OTHER INFORMATION: X = Ser, Tyr, Thr or Ala
<220> FEATURE:
<221> NAME/KEY: MISC_FEATURE
<222> LOCATION: (7)..(7)
<223> OTHER INFORMATION: X = Ser, Tyr, Asp, Val, Pro, Ala, His, Asn or
      Thr
<220> FEATURE:
<221> NAME/KEY: MISC_FEATURE
<222> LOCATION: (8)..(8)
<223> OTHER INFORMATION: X = Leu, Met, Gln, Arg or Lys
<220> FEATURE:
<221> NAME/KEY: MISC_FEATURE
<222> LOCATION: (9)..(9)
<223> OTHER INFORMATION: X = Glu, Gly or Arg
<220> FEATURE:
<221> NAME/KEY: MISC_FEATURE
<222> LOCATION: (11)..(11)
<223> OTHER INFORMATION: X = Lys, Met, Ala, Val, Leu, Ile, Phe, Pro, or
      Trp

<400> SEQUENCE: 42

Arg Xaa Cys Xaa Xaa Xaa Xaa Xaa Xaa Cys Xaa Lys Asp Ser Asp Cys
1               5                   10                  15

```
Leu Ala Glu Cys Val Cys Leu Glu His Gly Tyr Cys Gly
            20                  25

<210> SEQ ID NO 43
<211> LENGTH: 11
<212> TYPE: PRT
<213> ORGANISM: Artificial Sequence
<220> FEATURE:
<223> OTHER INFORMATION: tPA binding peptide
<220> FEATURE:
<221> NAME/KEY: MISC_FEATURE
<222> LOCATION: (2)..(2)
<223> OTHER INFORMATION: X = Trp or Leu
<220> FEATURE:
<221> NAME/KEY: MISC_FEATURE
<222> LOCATION: (4)..(4)
<223> OTHER INFORMATION: X = Pro, Ser, Thr or Ile
<220> FEATURE:
<221> NAME/KEY: MISC_FEATURE
<222> LOCATION: (5)..(5)
<223> OTHER INFORMATION: X = Arg, Lys or Thr
<220> FEATURE:
<221> NAME/KEY: MISC_FEATURE
<222> LOCATION: (6)..(6)
<223> OTHER INFORMATION: X = Ser, Tyr, Thr or Ala
<220> FEATURE:
<221> NAME/KEY: MISC_FEATURE
<222> LOCATION: (7)..(7)
<223> OTHER INFORMATION: X = Ser, Tyr, Asp, Val, Pro, Ala, His, Asn or
      Thr
<220> FEATURE:
<221> NAME/KEY: MISC_FEATURE
<222> LOCATION: (8)..(8)
<223> OTHER INFORMATION: X = Leu, Met, Gln, Arg or Lys
<220> FEATURE:
<221> NAME/KEY: MISC_FEATURE
<222> LOCATION: (9)..(9)
<223> OTHER INFORMATION: X = Glu, Gly or Arg
<220> FEATURE:
<221> NAME/KEY: MISC_FEATURE
<222> LOCATION: (11)..(11)
<223> OTHER INFORMATION: X = Lys, Met, Ala, Val, Leu, Ile, Phe, Pro or
      Trp

<400> SEQUENCE: 43

Arg Xaa Cys Xaa Xaa Xaa Xaa Xaa Xaa Cys Xaa
1               5                   10
```

PURIFICATION OF TISSUE PLASMINOGEN ACTIVATOR (TPA)

This application is a division of U.S. application Ser. No. 09/497,435, filed Feb. 3, 2000, now U.S. Pat. No.: 6,462,172, which is a division of U.S. Ser. No. 08/821,744, filed Mar. 20, 1997, now U.S. Pat. No. 6,084,062, which is a continuation-in-part of U.S. Ser. No. 08/619,885, filed Mar. 20, 1996, now abandoned.

FIELD OF THE INVENTION

The present invention relates to the field of protein purification. Specifically, the present invention relates to discovery of and isolation of affinity ligands useful for the purification of tissue plasminogen activator, or tPA.

BACKGROUND OF THE INVENTION

Human tissue-type plasminogen activator, or tPA, is a proteolytic enzyme produced by endothelial cells which has high affinity for fibrin contained in aggregates of coagulated blood (i.e., clots, or "thrombi"). tPA also serves to activate and convert plasminogen, an inactive proenzyme, into plasmin, a thrombolytic enzyme. Since tPA binds to fibrin in thrombi and activates plasminogen there to dissolve clots, tPA has become an important drug for use as a thrombolytic.

Although tPA has become a leading drug in the treatment of thrombosis, it competes against other effective thrombolytic agents, such as streptokinase and urokinase, which are arguably less effective but cost much less. In order for tPA to remain among the most-prescribed thrombolytic agents or to be distributed to even greater numbers of patients, ways in which tPA can be produced more efficiently or at lower cost must be explored.

Effective means for eliminating impurities such as cell debris, pathogens, non-human proteins, etc. from a production feed stream is also important in the production of tPA, as it is with any protein product intended ultimately for therapeutic administration to human patients.

Thus, there is a continuing need for the development of improved reagents, materials and techniques for the isolation of tPA on a more efficient and cost-effective basis.

Affinity chromatography is a very powerful technique for achieving dramatic single-step increases in purity. Narayanan (1994), for instance, reported a 3000fold increase in purity through a single affinity chromatography step.

Affinity chromatography is not, however, a commonly used technique in large-scale production of biomolecules. The ideal affinity chromatography ligand must, at acceptable cost, (1) capture the target biomolecule with high affinity, high capacity, high specificity, and high selectivity, (2) either not capture or allow differential elution of other species (impurities); (3) allow controlled release of the target under conditions that preserve (i.e., do not degrade or denature) the target; (4) permit sanitization and reuse of the chromatography matrix; and (5) permit elimination or inactivation of any pathogens. However, finding high-affinity ligands of acceptable cost that can tolerate the cleaning and sanitization protocols required in pharmaceutical manufacturing has proved difficult (see, Knight, 1990).

Murine monoclonal antibodies (MAbs) have been used effectively as affinity ligands. Monoclonal antibodies, on the other hand, are expensive to produce, and they are prone to leaching and degradation under the cleaning and sanitization procedures associated with purification of biomolecules, leading MAb-based affinity matrices to lose activity quickly (see, Narayanan, 1994; Boschetti, 1994). In addition, although MAbs can be highly specific for a target, the specificity is often not sufficient to avoid capture of impurities that are closely related to the target. Moreover, the binding characteristics of MAbs are determined by the immunoglobulin repertoire of the immunized animal, and therefore practitioners must settle for the binding characteristics they are dealt by the animal's immune system, i.e., there is little opportunity to optimize or select for particular binding or elution characteristics using only MAb technology. Finally, the molecular mass per binding site (25 kDa to 75 kDa) of MAbs and even MAb fragments is quite high.

Up until now, there have been no known affinity ligands suitable for the purification of tPA that approach the characteristics of the ideal affinity ligand described above, that not only bind to the target tPA molecule with high affinity but also release the tPA under desirable or selected conditions, that are able to discriminate between the tPA and other components of the solution in which the tPA is presented, and/or that are able to endure cleaning and sanitization procedures to provide regenerable, reusable chromatographic matrices.

Such tPA affinity ligands and methods for obtaining them are provided herein.

SUMMARY OF THE INVENTION

The present invention provides methods for obtaining affinity ligands for tPA which exhibit desirable or selected binding properties and release properties. The affinity ligands of the present invention exhibit not only favorable binding characteristics for affinity separation of tPA but also desired release (elution) characteristics and other desired properties such as stability, resistance to degradation, durability, reusability, and ease of manufacture.

The tPA affinity ligands of the present invention may be initially identified from a peptide library, such as a phage display library, by a method comprising:

(a) selecting a first solution condition (i.e., the binding conditions) at which it is desired that an affinity ligand should bind to the tPA;

(b) selecting a second solution condition (i.e., the release conditions) at which it is desired that an affinity complex between the tPA and the affinity ligand will dissociate, wherein the second solution condition is different from the first solution condition;

(c) providing a library of analogues of a candidate binding domain, wherein each analogue differs from said candidate binding domain by variation of the amino acid sequence at one or more amino acid positions within the domain;

(d) contacting said library of analogues with tPA at the first solution condition, for sufficient time to permit analogue/tPA binding complexes to form;

(e) removing analogues that do not bind under the first solution condition;

(f) altering the conditions of the solution of contacting step (e) to the second solution condition; and (g) recovering the candidate binding analogues released under the second solution condition, wherein the recovered analogues identify isolated tPA affinity ligands.

Following this general procedure, several polypeptide affinity ligands for tPA have been isolated, as described in more detail below.

DETAILED DESCRIPTION OF THE PREFERRED EMBODIMENTS

Figure 1:
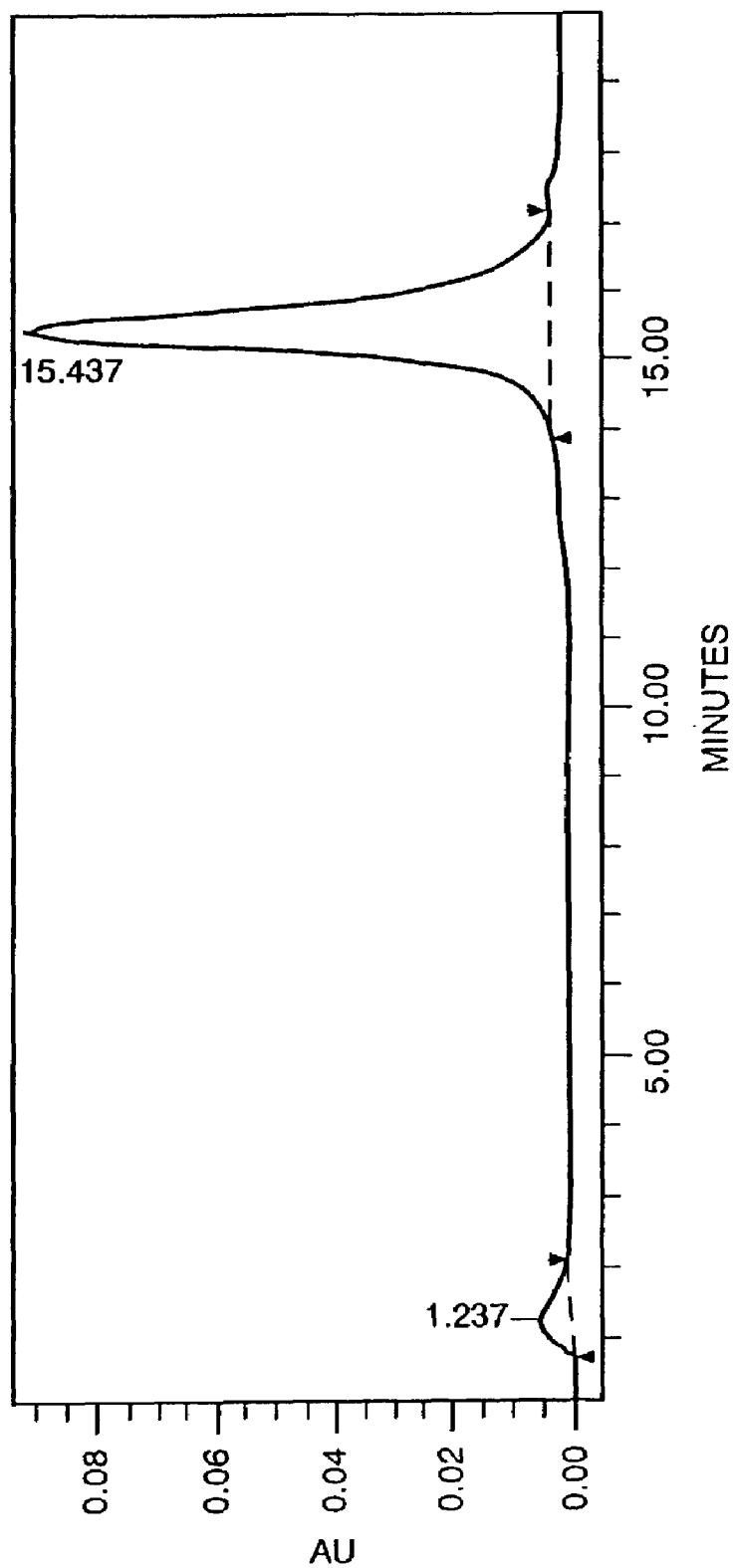
FIG. 1 shows a chromatogram of tissue plasminogen activator (25 μL of 1 mg/mL tPA) over an affinity chromatography column having an immobilized tPA affinity ligand (CMTI derivative #109, described in Example 1), with elution over a pH 7–pH 3 gradient. The peak at 15 minutes is estimated to contain approximately 90% of the injected tPA.
Figure 2:
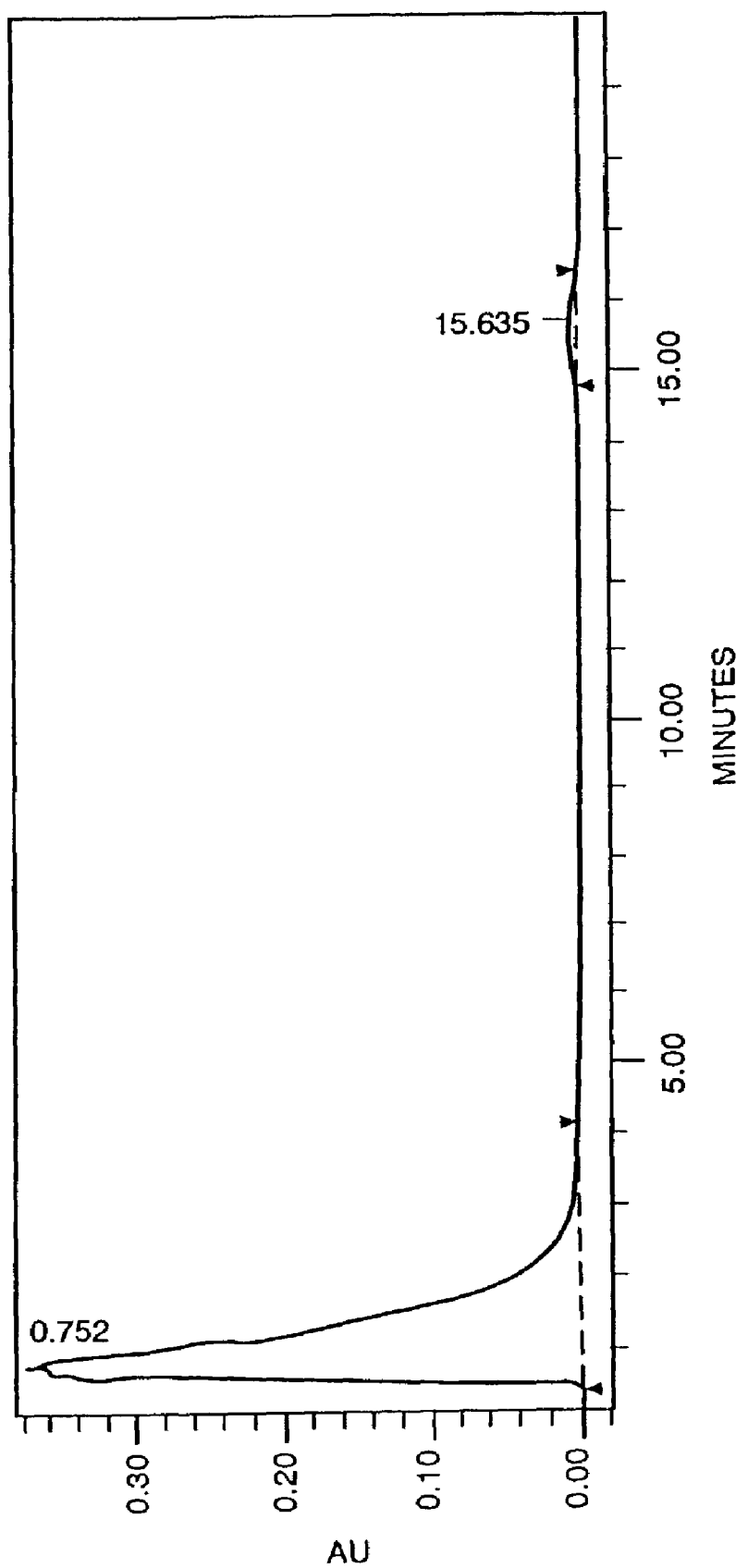
FIG. 2 shows a chromatogram of Coagulation Standard (diluted 10×) over a tPA affinity column (CMTI derivative #109) with elution as described above. The small peak at 15.6 minutes was shown to be a gradient artifact.

The present invention makes possible the efficient purification of tPA by affinity chromatography.

The tPA may be produced in any known way, including chemical synthesis; production in transformed host cells; secretion into culture medium by naturally occurring or recombinantly transformed bacteria, yeasts, fungi, insect cells, and mammalian cells; secretion from genetically engineered organisms (e.g., transgenic mammals); or in biological fluids or tissues such as urine, blood, milk etc. The solution that contains the crude tPA as it is initially produced (i.e., the production solution) will sometimes be referred to as the "feed stream".

Each method of producing tPA yields tPA in a feed stream that additionally contains a number of impurities (with respect to tPA). One purpose of the present invention is to produce affinity ligands and preparations (such as chromatography media) comprising such ligands that allow rapid and highly specific purification of tPA from any feed stream. The tPA affinity ligands obtained herein are tailored to the isolation of tPA from a particular feed stream, under specific preselected conditions. If an alternate production method for the tPA is used, producing a different feed stream, a different set of affinity ligands may be necessary to achieve the same level of purification. The new set of ligands can be readily obtained by following the procedures outlined herein.

tPA affinity ligands of the invention bind the tPA to the virtual exclusion of any other molecule in the feed stream with high affinity. Further, the affinity ligands release the tPA intact and in active form when the solution conditions are changed.

Selecting Binding and Release Conditions

In order to isolate new affinity ligands for tPA, two solution conditions are selected, i.e., binding conditions and release conditions. The binding conditions are a set of solution conditions under which it is desired that a discovered affinity ligand will bind the target tPA; the release conditions are a set of solutions conditions under which it is desired that a discovered affinity ligand will not bind the tPA. The two conditions may be selected to satisfy any criterion of the practitioner, such as ease of attaining the conditions, compatability with other purification steps, lowered cost of switching between conditions compared to other affinity media, etc. Preferably the two solution conditions are (a) well within the boundaries of the stability envelope for the tPA and (b) far apart with respect to at least one solution parameter. For example, if the tPA is stable over a wide pH range, then favorable binding conditions might be pH 7.5, 150 mM salt, 25° C. and favorable release conditions might be pH 3, 150 mM salt, 25° C. For a different tPA form having a narrow range of pH stability (for example, pH 6.2 to 7.8) but being stable over a wide range of salinity, two useful conditions might be binding conditions: pH 7.2, 3 M NaCl, 25° C. and release conditions: pH 7.2, 2 mM NaCl, 25° C.

Selection of a Candidate Binding Domain

In conjunction with selecting specific solution conditions for the desired binding and release of the tPA, a candidate binding domain is selected to serve as a structural template for the engineered affinity ligands that will exhibit the desired binding and release capabilities. The binding domain may be a naturally occurring or synthetic protein, or a region or domain of a protein. The candidate binding domain may be selected based on knowledge of a known interaction between the candidate binding domain and the tPA, but this is not critical. In fact, it is not essential that the candidate binding domain have any affinity for tPA at all: Its purpose is to provide a structure from which a multiplicity (library) of analogues can be generated, which multiplicity of analogues will include one or more analogues that exhibit the desired binding and release properties (and any other properties selected for). Thus, the binding conditions and the release conditions discussed infra may be selected with knowledge of the exact polypeptide that will serve as the candidate binding domain, or with knowledge of a class of proteins or domains to which the candidate binding domain belongs, or completely independently of the choice of the candidate binding domain. Similarly, the binding and/or release conditions may be selected with regard to known interactions between a binding domain and the tPA, e.g., to favor the interaction under one or both of the solution conditions, or they may be selected without regard to such known interactions. Likewise, the candidate binding domain can be selected taking into account the binding and/or release conditions or not, although it must be recognized that if the binding domain analogues are unstable under the binding or release conditions no useful affinity ligands will be obtained.

In selecting a candidate binding domain, the object is to provide a template or parental structure from which a library of similarly structured analogue domains can be generated. The analogue library will preferably be a biased library (as opposed to a randomly generated library), in that variegation of the basic domain to create the library will be carried out in such a way as to favor the properties desired for the affinity ligands.

The nature of the candidate binding domain greatly influences the properties of the derived proteins (analogues) that will be tested against the tPA molecule. In selecting the candidate binding domain, the most important consideration is how the analogue domains will be presented to the tPA, i.e., in what conformation the tPA and the analogues will come into contact. In preferred embodiments, for example, the analogues will be generated by insertion of synthetic DNA encoding the analogue into a replicable genetic package, resulting in display of the domain on the surface of a microorganism, such as M13 phage, using techniques as described, e.g., in U.S. Pat. No. 5,403,484 (Ladner et al.) and U.S. Pat. No. 5,223,409 (Ladner et al.), incorporated herein by reference.

Structured polypeptides offer many advantages as candidate binding domains over unstructured peptides. Mutation of surface residues in a protein will usually have little effect on the overall structure or general properties (such as size, stability, temperature of denaturation) of the protein; while at the same time mutation of surface residues may profoundly affect the binding properties of the protein. This has been fully documented, for example, for BPTI-homologous Kunitz domains (see Ladner, 1995). Mutating surface residues on proteins or structured domains can lead to greater diversity of properties for the analogues than is obtained by mutating unstructured peptides because the protein framework or the structure of the domain holds the mutated residues in conformations that differ from residue to residue and from framework to framework. This is especially important for hydrophobic side groups that would become buried unless constrained in a structure. The more tightly a peptide segment (domain) is constrained, the less likely it is to bind to any particular target. If it does bind, however, the binding is likely to be tighter and more specific. Thus, it is preferred to select a candidate binding domain and, in turn, a structure for the peptide analogues, that is constrained within a framework having some degree of rigidity. Alternatively, more than one candidate binding domain structure can be selected, in order to increase the size of the library of analogues and to introduce additional variegated structures for presentation to the tPA. As the size of the library is increased, and higher numbers and diversely structured analogues are prepared, the probability of including a useful framework and displayed functional groups increases to the point where high-affinity ligands can be found for isolation of the tPA from virtually any feed stream.

The size of the candidate binding domain is also an important consideration. Small proteins or polypeptides offer several advantages over large proteins, such as monoclonal antibodies (see Ladner, 1995). First, the mass per binding site is reduced. Highly-stable protein domains having low molecular weights, e.g., Kunitz domains (~7 kDa), Kazal domains (~7 kDa), *Cucurbida maxima* trypsin inhibitor (CMTI) domains (~3.5 kDa), and endothelin (~2 kDa), can show much higher binding per gram than do antibodies (150 kDa) or single-chain antibodies (30 kDa).

Second, the possibility of non-specific binding is reduced because there is less surface available.

Third, small proteins or polypeptides can be engineered to have unique tethering sites in a way that is impracticable for antibodies. For example, small proteins can be engineered to have lysines only at sites suitable for tethering (e.g., to a chromatography matrix), but this is not feasible for antibodies. It is often found that only a small fraction of immobilized antibodies are active, possibly due to inappropriate linkage to the support.

Most small proteins or polypeptides that are stabilized by disulfides do not contain cysteines that are not involved in disulfides. This is because the oxidizing conditions that cause disulfide formation for stabilizing the protein also lead to disulfide formation by otherwise unpaired cysteines. Thus, small proteins having stabilizing disulfides and an odd number of cysteines tend to form disulfide linked dimers (e.g., homodimers or heterodimers). The disulfides between domains are more easily reduced than are the stabilizing intradomain disulfides. Thus, by selective reduction it is possible to obtain monomeric disulfide-stabilized domains having a single free thiol. Such thiols can be used for highly stable immobilization of these domains by formation of a thioether with iodoaceamide, iodoacetic acid, or similar α-iodo carboxylic acid groups.

Small protein or polypeptide domains also can be chemically synthesized, which permits special immobilizing groups to be incorporated in a way that does not interfere with binding to the tPA. For instance, if small disulfide-containing proteins are chemically synthesized, the amino acid sequence can be altered by adding an extra cysteine residue with the thiol blocked in a different manner from other cysteines elsewhere in the sequence. The selected thiols can be deblocked and disulfides allowed to form, then the added cysteine can be deblocked and the molecule can be immobilized by reaction with a suitable material such as a substrate containing immobilized $NH_2$—CO—$CH_2I$.

Fourth, a constrained polypeptide structure is more likely to retain its functionality when transferred with the structural domain intact from one framework to another. For instance, the binding domain structure is likely to be transferable from the framework used for presentation in a library (e.g., displayed on a phage) to an isolated protein removed from the presentation framework or immobilized on a chromatographic substrate.

There are many small, stable protein domains suitable for use as candidate binding domains and for which the following useful information is available: (1) amino acid sequence, (2) sequences of several homologous domains, (3) 3-dimensional structure, and (4) stability data over a range of pH temperature, salinity, organic solvent, oxidant concentration. Some examples are: Kunitz domains (58 amino acides, 3 disulfide bonds), *Cucurbida maxima* trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), and Streptococcal G IgG-binding domain (35 amino acids, no disulfide bonds). Most, but not all of these contain disulfide bonds that rigidify and stabilize the structure. Libraries based on each of these domains, preferably displayed on phage or other genetic packages, can be readily constructed and used for the selection of binding analogues.

Providing a Library of Candidate Binding Domain Analogues

Once a candidate binding domain has been selected, a library of potential affinity ligands is created for screening against the tPA at the binding and elution (release) conditions. The library is created by making a series of analogues, each analogue corresponding to the candidate binding domain except having one or more amino acid substitutions in the sequence of the domain. The amino acid substitutions are expected to alter the binding properties of the domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). Most preferably the amino acid positions to be varied will be adjacent or close together, so as to maximize the effect of substitutions. In addition, extra amino acids can be added into the structure of the candidate binding domain.

In preferred embodiments, especially where a great deal of information is available concerning the interactions of the tPA with other molecules, particularly the candidate binding domain, those amino acid positions that are essential to binding interactions will be determined and conserved in the process of building the analogue library (i.e., the amino acids essential for binding will not be varied).

The object of creating the analogue library is to provide a great number of potential affinity ligands for reaction with the tPA molecule, and in general the greater the number of analogues in the library, the greater the likelihood that a member of the library will bind to the tPA and release under the preselected conditions desired for release. On the other hand, random substitution at only six positions in an amino acid sequence provides over 60 million analogues, which is a library size that begins to present practical limitations even when utilizing screening techniques as powerful as phage display. It is therefore preferred to create a biased library, in which the amino acid positions designated for variation are considered so as to maximize the effect of substitution on the binding characteristics of the analogue, and the amino acid residues allowed or planned for use in substitutions are limited to those that are likely to cause the analogue to be responsive to the change in solution conditions from the binding conditions to the release conditions.

As indicated previously, the techniques discussed in U.S. Pat. No. 5,223,409 are particularly useful in preparing a library of analogues corresponding to a selected candidate binding domain, which analogues will be presented in a form suitable for large-scale screening of large numbers of analogues with respect to a target tPA molecule. The use of replicable genetic packages, and most preferably phage display, is a powerful method of generating novel polypeptide binding entities that involves introducing a novel DNA segment into the genome of a bacteriophage (or other amplifiable genetic package) so that the polypeptide encoded by the novel DNA appears on the surface of the phage. When the novel DNA contains sequence diversity, then each recipient phage displays one variant of the initial (or "parental") amino acid sequence encoded by the DNA, and the phage population (library) displays a vast number of different but related amino acid sequences.

A phage library is contacted with and allowed to bind the tPA molecule, and non-binders are separated from binders. In various ways, the bound phage are liberated from the tPA and amplified. Since the phage can be amplified through infection of bacterial cells, even a few binding phage are sufficient to reveal the gene sequence that encodes a binding entity. Using these techniques it is possible to recover a binding phage that is about 1 in 20 million in the population. One or more libraries, displaying 10–20 million or more potential binding polypeptides each, can be rapidly screened to find high-affinity tPA ligands. When the selection process works, the diversity of the population falls with each round until only good binders remain, i.e., the process converges. Typically, a phage display library will contain several closely related binders (10 to 50 binders out of 10 million). Indications of convergence include increased binding (measured by phage titers) and recovery of closely related sequences. After a first set of binding polypeptides is identified, the sequence information can be used to design other libraries biased for members having additional desired properties, e.g., discrimination between tPA and particular fragments.

Such techniques make it possible not only to screen a large number of analogues but make it practical to repeat the binding/elution cycles and to build secondary, biased libraries for screening analog-displaying packages that meet initial criteria. Thus, it is most preferred in the practice of the present invention (1) that a library of binding domain analogues is made so as to be displayed on replicable genetic packages, such as phage; (2) that the library is screened for genetic packages binding to tPA wherein the binding conditions of the screening procedure are the same as the binding conditions preselected for the desired affinity ligand; (3) that genetic packages are obtained by elution under the release conditions preselected for the affinity ligand and are propagated; (4) that additional genetic packages are obtained by elution under highly disruptive conditions (such as, e.g., pH 2 or lower, 8 M urea, or saturated guanidinium thiocyanate, to overcome extremely high affinity associations between some displayed binding domain analogues and the target tPA) and are propagated; (5) that the propagated genetic packages obtained in (3) or (4) are separately or in combination cycled through steps (2) and (3) or (4) for one or more additional cycles; and (6) a consensus sequence of high-affinity binders is determined for analogues expressed in genetic packages recovered from such cycles; (7) that an additional biased library is constructed based on the original framework (candidate binding domain) and allowing the high-affinity consensus at each variable amino acid position, and in addition allowing other amino acid types selected to include amino acids believed to be particularly sensitive to the change between the binding conditions and the release conditions; (8) that this biased library is screened for members that (a) bind tightly (i.e., with high affinity) under the binding conditions and (b) release cleanly (i.e., readily dissociate from the tPA target) under the release conditions.

Use of the Affinity Ligands in Chromatography

After members of one or more libraries are isolated that bind to a tPA with desired affinity under binding conditions and release from the tPA as desired under release conditions, isolation of the affinity ligands can be accomplished in known ways. If, for example, the analogue library is composed of prospective affinity ligands expressed on phage, released phage can be recovered, propagated, the synthetic DNA insert encoding the analogue isolated and amplified, the DNA sequence analyzed and any desired quantity of the ligand prepared, e.g., by direct synthesis of the polypeptide or recombinant expression of the isolated DNA or an equivalent coding sequence.

Additional desired properties for the ligand can be engineered into an analogue ligand in the same way release properties were engineered into the ligand, by following similar steps as described above.

The affinity ligands thus isolated will be extremely useful for isolation of tPA by affinity chromatography methods. Any conventional method of chromatography may be employed. Preferably, an affinity ligand of the invention will be immobilized on a solid support suitable, e.g., for packing a chromatography column. The immobilized affinity ligand can then be loaded or contacted with a feed stream under conditions favorable to formation of ligand/tPA complexes, non-binding materials can be washed away, then the tPA can be eluted under conditions favoring release of the tPA molecule from a ligand/tPA complex. Alternatively, bulk chromatography can be carried out by adding a feed stream and an appropriately tagged affinity ligand together in a reaction vessel, then isolating complexes of the tPA and ligand by making use of the tag (e.g., a polyHis affinity tag, which can by used to bind the ligand after complexes have formed), and finally releasing the tPA from the complex after unbound materials have been eliminated.

It should be noted that although precise binding and release properties are engineered into the affinity ligands, subsequent use in affinity purification may reveal more optimal binding and release conditions under which the same isolated affinity ligand will operate. Thus, it is not critical that the affinity ligand, after isolation according to this invention, be always employed only at the binding and release conditions that led to its separation from the library.

Finally, it should be kept in mind that the highest affinity ligand is not necessarily the best for controllable or cost-effective recovery of a tPA molecule. The method of the invention permits selection of ligands that have a variety of desirable characterists important to the practitioner seeking isolation of tPA from a particular feed steam, such as specific binding of the tPA coupled with predictable and controlled, clean release of the tPA, useful loading capacity, acceptably complete elution, re-usability/recyclability, etc.

Isolation of tPA affinity ligands in accordance with this invention will be further illustrated below. The specific parameters included in the following examples are intended to illustrate the practice of the invention, and they are not presented to in any way limit the scope of the invention.

EXAMPLE 1

The techniques described above were employed to isolate affinity ligands for recombinant human tissue-type plasminogen activator (tPA). The process of creating tPA affinity ligands involved three general steps: (1) screening of approximately 11 million variants of a stable parental protein domain for binding to tPA, (2) producing small quantities of the most interesting ligands, and (3) chromatographic testing of one ligand bound to activated beads for the affinity purification of tPA from a plasma spiked sample.

For this work, tPA was purchased from CalBiochem (#612200) and immobilized on ReactiGel™ agarose beads from Pierce Chemical Company by methods described in Markland et al. (1996). Approximately 200 µg of tPA were coupled to 200 µL of ReactiGel™ slurry.

Four libraries of phage-displayed proteins were picked for the screening process. Three were based on the first Kunitz domain of lipoprotein associated coagulation inhibitor (LACI-K1), called Lib#1, Lib#3, and Lib#5 and one was based on *Cucurbida maxima* trypsin inhibitor I (CMTI-I). CMTI-I is a protein found in squash seeds and is able to withstand the acidic and proteolytic conditions of the gut. These proteins each have three disulfide bridges, making them highly constrained and stable. Members of these protein families have been shown to have outstanding thermal stability (>80° C. without loss of activity), outstanding pH stability (no loss of activity on overnight incubation at pH 2 and 37° C. or on 1 hour exposure to pH 12 at 37° C.), and outstanding stability to oxidation. The number of potential amino acid sequences in each library is given in Table 1 below:

TABLE 1

Phage display library populations used in the tPA screening

| Library name | parental domain | Number of members |
|---|---|---|
| Lib#1 | LACI-K1 | 31,600 |
| Lib#3 | LACI-K1 | 516,000 |
| Lib#5 | LACI-K1 | 1,000,000 |
| CMTI | CMTI-I | 9,500,000 |
| Total | | 11,000,000 |

The total diversity of the phage-display libraries screened against tPA in this work is estimated to be around 11 million. The Kunitz domain and the CMTI domain could display much greater diversity by varying other parts of their surfaces.

Two screening protocols were used: "slow screen" and "quick screen". In a slow screen, phage from each round were amplified in *E. coli* before the next round. In a quick screen, phage recovered from the tPA in one round served as the input for the next round without amplification. In a quick screen, both the input and recovered number of phage decreased rapidly over several rounds. The input level can be kept constant in a slow screen. The constant input in a slow screen allows comparisons between rounds that can indicate selection or lack thereof, but comparisons between rounds of quick screens are difficult to interpret. Quick screening increases the likelihood that phage will be selected for binding rather than other irrelevant properties (e.g., infectivity or growth rates).

The phage libraries described were screened for binding to tPA through four rounds. In the first round, the phage libraries were mixed in separate reactions with tPA agarose beads at pH 7 in phosphate-buffered saline (PBS). Bovine serum albumin (BSA) was added at 0.1% to reduce non-specific binding. Unbound phage were washed off at pH 7, and the bound phage eluted at pH 2 for the first screen only. The subsequent three quick screens had a different elution protocol and used pooled outputs of the first screen. Pool A consisted of the combined outputs from the CMTI and Lib#1 libraries, and Pool B consisted of the combined outputs of the Lib#3 and Lib#5 libraries. The binding of pooled libraries was performed at pH 7, however, the first elution to remove bound phage was carried out at pH 5 and a subsequent elution at pH 2 to elute phage that are released in the pH 5–pH 2 range. This was repeated twice more for a total of 4 rounds of selection.

The phage titers from the final three rounds of screening are shown below in Table 2. The output of one round was the input to the next round.

TABLE 2

Phage titers prior to screening and after the last three rounds of screening libraries against tPA

| | Pool A pH 5 elution | Pool A pH 2 elution | Pool B pH 5 elution | Pool B pH 2 elution |
|---|---|---|---|---|
| Prior to Quick Screening | $7 \times 10^{11}$ | $7 \times 10^{11}$ | $5 \times 10^{11}$ | $5 \times 10^{11}$ |
| After second round | $1 \times 10^8$ | $3 \times 10^7$ | $7 \times 10^6$ | $3 \times 10^6$ |
| After third round | $2 \times 10^5$ | $2 \times 10^6$ | $2 \times 10^3$ | $7 \times 10^3$ |
| After fourth round | $3 \times 10^4$ | $2 \times 10^5$ | 150 | 90 |

From the phage titers, it is appears that Pool A converged and contains strong binders, whereas Pool B had neither significant convergence nor strong binders.

Forty phage clones were selected from the third round quick screen selectants of each pool for further analysis, 20 from the pH 5 pool and 20 from the pH 2 pool. The phage DNA was amplified using PCR to determine whether CMTI- or LACI-derived gene fragments were present.

CMTI-derived gene constructs were found in 38 out of 40 phage isolates from the quick screen of pool A. The remaining isolates did not yield a PCR product, indicating a deletion. Only 10 of the 40 phage isolates from the quick screen of pool B contained the appropriate construct, another indication that the search had not succeeded.

One sign that a particular phage-displayed protein has a high affinity for the tPA molecule is that it is found repeatedly. From the 18 CMTI-derived phage isolates that release at pH 2, one sequence was found five times, a second, four times, and two of the remaining occurred three times. The 18 sequences formed a closely-related family of selected molecules, a further sign that the search had successfully converged.

Table 3 shows the variability of the observed sequences as a function of the permitted variability and the selection pH. The CMTI library was constructed by introducing combinatorial sequence diversity into codons specifying a surface-exposed loop formed between cysteines 3 and 10 of the parental CMTI protein. The cysteines were not varied because they form an important part of the structure.

Table 3 shows the DNA sequence of the CMTI library. Residues $F_{-5}$ and $Y_{-4}$ correspond to residues 14 and 15 in the signal sequence of M13mp18 from which the recipient phage was engineered. Cleavage by Signal Peptidase I (SP-I) is assumed to occur between $A_1$ and $R_1$. Residues designated 100–113 make up a linker between the CMTI variants and mature III, which begins with residue $A_{201}$. The amino acid sequence $Y_{104}$IEGRIV should allow specific cleavage of the linker with bovine Factor $X_a$ between $R_{108}$ and $I_{109}$. The M13-related phage in which this library was constructed carries an ampicillin-resistance gene ($Ap^R$) so that cells infected by library phage become Ap resistant. At each variable amino acid position, the wild-type amino acid residue is shown underscrored. The amino acid sequence shown in Table 3 is designated SEQ ID NO: 2; the nucleotide sequence shown in Table 3 is designated SEQ ID NO: 3.

TABLE 3

Construction of CMTI Library by Variegation of CMTI-I
framework sequence: CMTI-I = RVCPR ILMEC KKDSD CLAEC VCLEH GYCG
(SEQ ID NO: 1)
(see, Dung, L-N. et al., Int'l J. Peptide Protein Res., 34: 492–497 (1989))

| amino acids encoded (SEQ ID NO: 2) | F | Y | S | G | A | R | LSWP QRM TK<u>V</u>A EG | C | FSYC L<u>P</u>HR ITNV ADG |
|---|---|---|---|---|---|---|---|---|---|
| codon position | −5 | −4 | −3 | −2 | −1 | 1 | 2 | 3 | 4 |
| codons (SEQ ID NO: 3) | TTC | TAT | TCC | GGA | GCC | CGT | NNG | TGT | NNT |
| restriction sites or position | | | └─AccIII─┘ | | | | | P3 | P2 |

| amino acids encoded | K<u>R</u><u>T</u>I | FSYC L<u>P</u>HR <u>I</u>TNV ADG | FSYC L<u>P</u>HR <u>I</u>TNV ADG | LSWP QR<u>M</u> TKVA EG | E<u>K</u>RG | C | K | K | D |
|---|---|---|---|---|---|---|---|---|---|
| codon position | 5 | 6 | 7 | 8 | 9 | 10 | 11 | 12 | 13 |
| codons | ANA | NNT | NNT | NNG | RRG | TGT | AAG | AAG | GAT |
| restriction sites or position | P1 | P1' | P2' | P3' | | | | | |

| amino acids encoded | S | D | C | L | A | E | C | V | C |
|---|---|---|---|---|---|---|---|---|---|
| codon position | 14 | 15 | 16 | 17 | 18 | 19 | 20 | 21 | 22 |
| codons | TCT | GAT | T GC | TTA | GC A | GAA | TGC | GTT | TGC |
| restriction sites or position | | | └────EspI────┘ | | | | | | |

| amino acids encoded | L | E | H | G | Y | C | G | A | G |
|---|---|---|---|---|---|---|---|---|---|
| codon position | 23 | 24 | 25 | 26 | 27 | 28 | 29 | 100 | 101 |
| codons | CTC | GAG | CAT | GGT | TAT | TGT | GGC | GCC | GGT |
| restriction sites or position | └─XhoI─┘ | | | | | | └─KasI─┘ | | |

| amino acids encoded | P | S | Y | I | E | G | R | I | V |
|---|---|---|---|---|---|---|---|---|---|
| codon position | 102 | 103 | 104 | 105 | 106 | 107 | 108 | 109 | 110 |
| codons | CCT | TCA | TAC | ATT | GAA | GGT | CGT | ATT | GTC |
| restriction sites or position | | | | | | | | | |

| amino acids encoded | G | S | A | A | E | . . . rest of mature III | | | |
|---|---|---|---|---|---|---|---|---|---|
| codon position | 111 | 112 | 113 | 201 | 202 | | | | |
| codons | GGT | AGC | GCC | GCT | GAA | . . . rest of coding sequence for III | | | |
| restriction sites or position | | | | | | | | | |

This gives $9.13 \times 10^6$ protein sequences and $16.8 \times 10^6$ DNA sequences.

The isolates obtained from the pH 5 selection procedure exhibited greater sequence diversity than did the pH 2 selectants (Table 4). Despite the greater sequence variability, pH 5 selectants comprised a family of closely-related protein sequences. Forming all combinations of the amino-acid types observed at each position gives only 13,400 (=2×4×3×4×7×5×4) which is 0.15% of the original population. In the 20 sequences determined, there were four sequences that occurred more than once, suggest that the actual diversity is less than 13,400. Although the family of pH 5-selected sequences is clearly related to the pH 2-selected family, there was only one example of sequence identity between the two sequence populations.

TABLE 4

Reduction in variability at positions in CMTI upon selection for binding to tPA

| Position: | 2 | 3 | 4 | 5 | 6 | 7 | 8 | 9 | 10 |
|---|---|---|---|---|---|---|---|---|---|
| Permitted Variability | 13 | C | 15 | 4 | 15 | 15 | 13 | 4 | C |
| Variability of pH 5 Selectants | 2 | C | 4 | 3 | 4 | 7 | 5 | 4 | C |
| Variability of pH 2 Selectants | 1 | C | 1 | 2 | 3 | 3 | 1 | 2 | C |

At positions 6 and 7, most (12 of 15) allowed amino acid types were rejected in the pH 2 selectants. From the selected sequences, it is not clear whether the selected amino acids at positions 6 and 7 contributed to binding or merely represent the elimination of unacceptable possibilities at these positions.

The powerful convergence of the selection process is particularly evident for the pH 2 selectants at positions 2, 4 and 8, where, although many amino acid types could occur, only one amino acid type was found. This is a strong indication that this specific amino acid is critical to binding. At each of these positions, the uniquely selected type of the pH 2 population was also the most common type at that position in the pH 5 population. Allowing all observed amino acid types at each position of the pH 2 pool gives only 36 sequences, 0.0004% of the initial population. That several sequences appeared more than once suggests the number of different sequences present in the pH 2 pool is not larger than 36.

Table 5 shows the amino acid sequences of the variegated region (amino acid positions 1–12) for the 38 sequenced analogues of CMTI-I. The appearance of methionine residues at a position not designed to be varied (position 11) indicates a DNA synthesis error in formation of the library.

TABLE 5

| | AMINO ACID position | | | | | | | | | | | | Residues 1–12 of SEQ ID |
|---|---|---|---|---|---|---|---|---|---|---|---|---|---|
| | 1 | 2 | 3 | 4 | 5 | 6 | 7 | 8 | 9 | 10 | 11 | 12 | |
| CMTI-I | R | V | C | P | R | I | L | M | E | C | K | K | 1 |
| 101 | R | W | C | P | K | T | S | L | G | C | M | K | 4 |
| 102 | R | L | C | P | K | T | Y | L | G | C | M | K | 5 |
| 103 | R | W | C | S | T | Y | S | L | G | C | M | K | 6 |
| 104 | R | W | C | S | T | Y | S | L | G | C | M | K | 7 |
| 105 | R | L | C | P | K | T | S | L | E | C | M | K | 8 |
| 106 | R | W | C | S | T | Y | S | L | G | C | M | K | 9 |

TABLE 5-continued

| | AMINO ACID position | | | | | | | | | | | | Residues 1–12 of SEQ ID |
|---|---|---|---|---|---|---|---|---|---|---|---|---|---|
| | 1 | 2 | 3 | 4 | 5 | 6 | 7 | 8 | 9 | 10 | 11 | 12 | |
| 107 | R | L | C | P | K | T | S | L | E | C | M | K | 10 |
| 108 | R | W | C | S | K | S | S | L | E | C | M | K | 11 |
| 109 | R | L | C | P | K | T | D | L | G | C | M | K | 12 |
| 110 | R | W | C | P | K | S | S | M | G | C | K | K | 13 |
| 111 | R | W | C | P | R | T | V | Q | E | C | M | K | 14 |
| 112 | R | W | C | P | T | A | P | L | E | C | M | K | 15 |
| 113 | R | L | C | P | K | T | D | L | G | C | M | K | 16 |
| 114 | R | W | C | P | K | S | A | L | D | C | K | K | 17 |
| 115 | R | W | C | T | K | T | S | R | E | C | M | K | 18 |
| 116 | R | W | C | I | R | T | D | L | G | C | M | K | 19 |
| 117 | R | W | C | P | K | T | S | L | G | C | M | K | 20 |
| 118 | R | W | C | P | R | T | V | R | R | C | M | K | 21 |
| 119 | R | W | C | P | K | T | H | K | E | C | M | K | 22 |
| 120 | R | W | C | P | K | T | S | L | E | C | M | K | 23 |
| 221 | R | W | C | P | K | S | T | L | G | C | M | K | 24 |
| 222 | R | W | C | P | K | S | T | L | G | C | M | K | 25 |
| 223 | R | W | C | P | K | Y | T | L | E | C | M | K | 26 |
| 224 | R | W | C | P | R | S | S | L | E | C | M | K | 27 |
| 225 | R | W | C | P | K | Y | T | L | E | C | M | K | 28 |
| 226 | R | W | C | P | R | S | N | L | E | C | M | K | 29 |
| 227 | R | W | C | P | R | S | N | L | E | C | M | K | 30 |
| 228 | R | W | C | P | K | Y | T | L | E | C | M | K | 31 |
| 229 | R | W | C | P | K | Y | T | L | E | C | M | K | 32 |
| 230 | R | W | C | P | K | Y | T | L | E | C | M | K | 33 |
| 231 | R | W | C | P | R | S | T | L | E | C | M | K | 34 |
| 232 | R | W | C | P | K | T | S | L | G | C | M | K | 35 |
| 233 | R | W | C | P | K | Y | T | L | E | C | M | K | 36 |
| 234 | R | W | C | P | R | S | S | L | E | C | M | K | 37 |
| 235 | R | W | C | P | K | S | T | L | G | C | M | K | 38 |
| 236 | R | W | C | P | R | S | L | E | C | M | K | 39 |
| 237 | R | W | C | P | R | S | N | L | E | C | M | K | 40 |
| 238 | R | W | C | P | R | S | N | L | E | C | M | K | 41 |

The specificity of phage-bound ligand candidates was tested by determining their affinity for other immobilized proteins. The phage bound proteins showed no affinity for the related human serum proteases plasmin and thrombin bound to beads (data not shown). Additionally, experiments were performed on the phage isolates to determine relative affinity for and release characteristics from immobilized tPA.

In the case of the pH 5-releasing phage isolates, the majority of the phage are released at pH 5 and an order of magnitude fewer are released by further dropping the pH to 2. This indicates suitable affinity ligands with a relatively dean release upon lowering the pH to 5. In the case of the pH 2 releasing isolates, only isolate #232 gave a truly selective binding at pH 5 and then release at pH 2.

Ligand Synthesis and Immobilization

Next, free CMTI-derivative polypeptides were synthesized using the sequence information determined from the DNA of the phage isolates. Although the CMTI derivatives (analogues) could have been readily chemically synthesized, it was decided to express the polypeptides in yeast. One of the pH 5-releasing isolates, #109 (Table 5; ref. SEQ ID NO. 12), and one of the pH 2-releasing isolates, #232 (Table 5; ref. SEQ ID NO. 35), were selected for expression in *Pichia pastoris*. At positions 4 and 8, isolate #109 has the same amino acid types as seer in the pH 2 selectants; at position 2, isolate #109 differs from the pH 2 selectants.

The appropriate gene constructs were synthesized and inserted into the *Pichia pastoris* expression system (Vedvick et al., 1991 and Wagner et al., 1992) to create production strains. Five-liter fermentations of each strain resulted in high-level expression. It was estimated that the proteins were secreted into the fermentation broth in excess of 1 g/L. The crude fermentation suspensions were clarified by centrifugation, and 0.2 μ microfiltration steps. The 0.2 μ filtrates were purified by ultrafiltration using PTTK cassettes with a 30 kDa NMWL cutoff. The ligands were purified from the ultrafiltration filtrates by cation exchange chromatography with Macro-Prep High S cation exchange support (BioRad), followed by two reversed-phase separations. The reversed-phase separations used a linear gradient starting with water containing 0.1% TFA and having increasing acetonitrile (containing 0.1% TFA) which was increased to 50% at 90 minutes. The resulting protein was more than 95% pure as measured by PDA spectral analysis on a 5 μm reversed phase column.

The ligand candidate was immobilized on a bis-acrylamide/azlactone copolymer support with immobilized diaminopropylamine (Emphaze Ultralink™, Pierce Chemical Co.) according to the manufacturer's instructions. About 30 mg of CMTI analogue #109 were coupled to 1 mL of the activated chromatography support.

Column Testing

A Waters AP Minicolumn, 5.0 cm×0.5 cm ID nominal dimensions was modified by the addition of a second flow adaptor which allowed the column length to be reduced to 2.5 cm. This column was packed with #109-Emphaze Utralink™ beads using the recommended protocol and washed using a series of increasing NaCl concentration washes at pH 7 concluding with a 1 M wash.

In a first test of the #109 affinity column tissue-type plasminogen activator obtained from CalBiochem was made up to manufacturer's specifications to provide a 1 mg/mL solution of tPA. Coagulation Standard (Coagulation Control Level 1 from Sigma Diagnostics, Catalog #C-7916) lyophilized human plasma, was reconstituted according to the manufacturer's instructions, then diluted 10× and the tPA added. This sample was loaded onto the column and eluted in the presence of 1 M NaCl in all buffers, which was sufficient to suppress non-specific protein binding to the column and to permit the pH-controlled binding and release of the tPA. There were two distinct peaks: The first contained the plasma proteins (which were not retained on the column); the second, obtained after lowering the pH, contained the tPA, without any Madrid plasma components. The results were confirmed by silver stained gel (not shown). 90% of the tPA product was recovered.

A second affinity column using the #109 CMTI analogue was prepared using EAH Sepharose 4B™ agarose beads (Pharmacia; Upsala SE) as the chromatography support. The separation was performed on an HPLC system manufactured by Waters Inc. (Milford, Mass.). The system comprised a Model 718 Autoinjector, a Model 600 solvent delivery system with pumpheads capable of delivering 20 mL/minute, and a Model 996 photodiode array detector. All of the equipment was installed according to manufacturer's specifications. The system was controlled by a Pentium 133 IBM-compatible computer supplied by Dell Corp. The computer was furnished with a 1 gigabyte hard drive, 16 megabytes of RAM, and a color monitor, onto which the Millenium software supplied by Waters Inc. was loaded.

Spectral data in the range 200 nm to 300 nm were collected with 1.2 nm resolution. FIGS. 1, 2, 3, and 4 were collected at 280 nm. The mobile phases for the chromatographic work were Buffer A and Buffer B: Buffer A consisted of 25mM potassium phosphate, 50 mM arginine, and 125 mM NaCl, buffered to pH 7 with potassium hydroxide. Buffer B consisted of 50 mM potassium phosphate and 150 mM NaCl, buffered to pH 3 with phosphoric acid. In all cases, samples were injected in 100% Buffer A, followed by washing with 100% Buffer A from t=0 to t=2 min. From t=2 min. to t=8 min., elution was with 100% Buffer B. After t=8 min., elution was with 100% Buffer A. The gradient delay volume of the HPLC system was approximately 4 mL and the flow rate was 0.5 mL/min.

tPA from another commercial source was made up to manufacturer's specifications to provide a 1 mg/mL solution. Coagulation Standard (Coagulation Control Level 1 from Sigma Diagnostics, Catalog #C-7916), lyophilized human plasma, was reconstituted according to the manufacturer's instructions. This solution was diluted 10:1 to obtain a solution having roughly 10 times the absorbance of the tPA solution.

Figure 3:
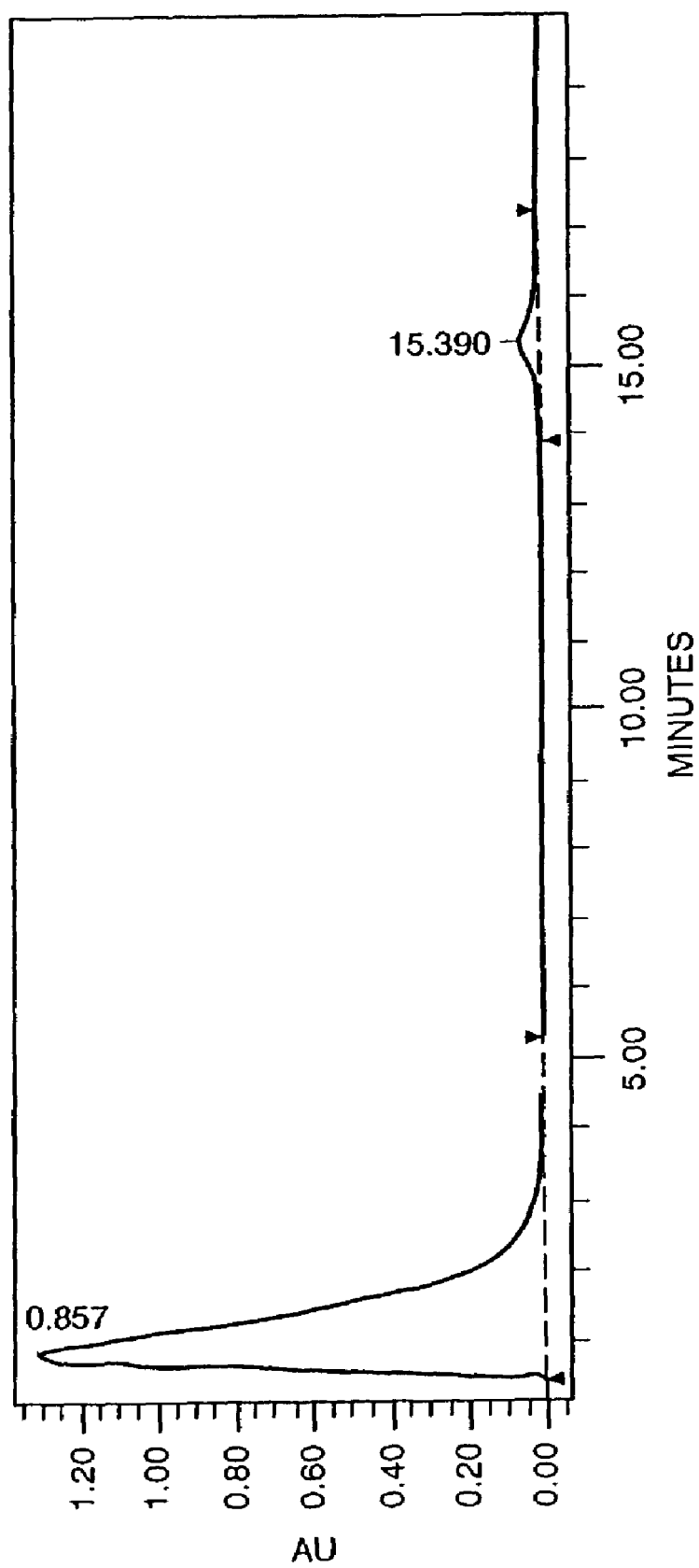
FIG. 3 shows a chromatogram of a mixture consisting of 25 μL of Coagulation Standard (Diluted 10×) spiked with 25 μL of tPA, with elution over a pH 7–pH 3 gradient. The peak at 1 minute is the collection of plasma proteins and the peak at 15.4 minutes is the tPA.
Figure 4:
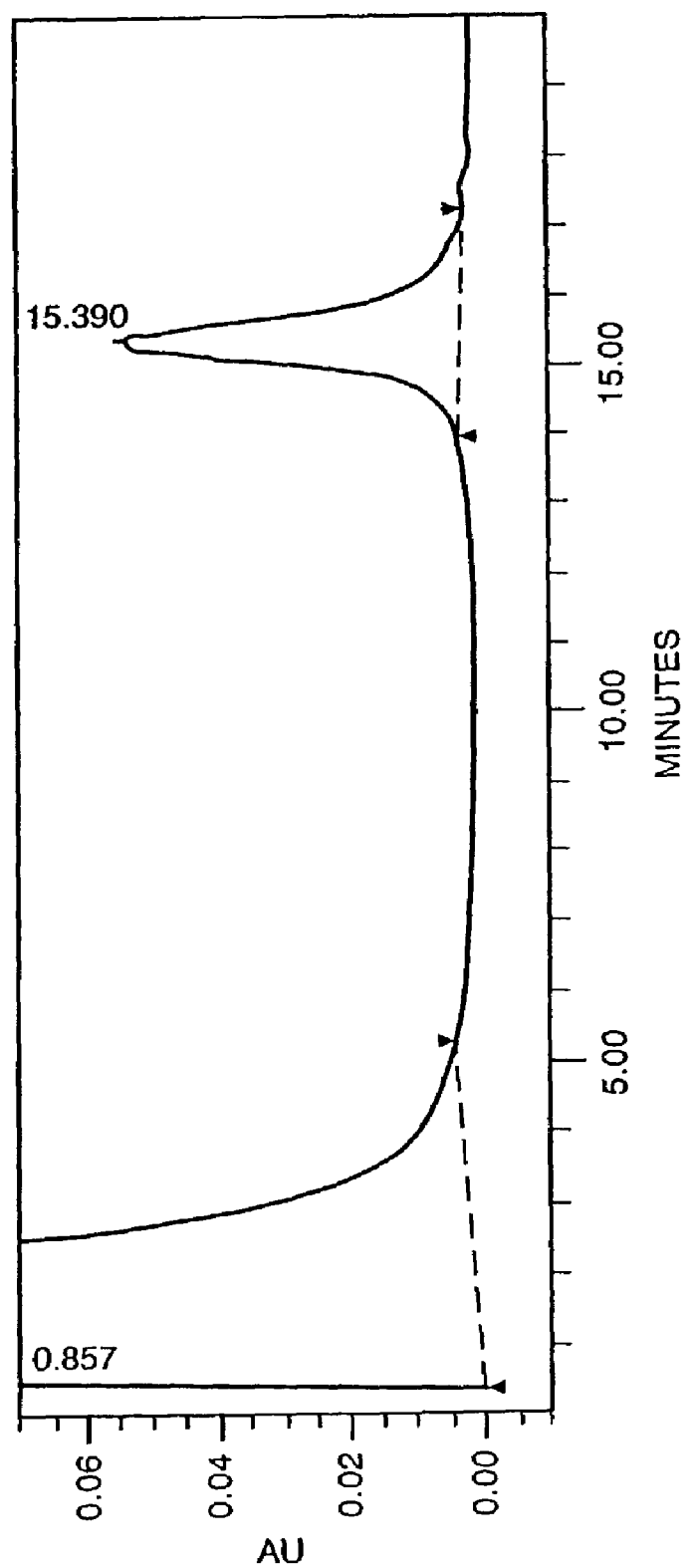
FIG. 4 shows the same chromatogram as shown in FIG. 3 with vertical scale expanded.

In the test shown in FIG. 1, a sample of pure tPA (25 μL of 1 mg/mL tPA) was run over the #109 CMTI derivative-containing column and eluted as described above. The chromatogram shows sharp elution of about 90% of the tPA material after about 15 min. In the test shown in FIG. 2, a sample of Coagulation Standard (10× dilution) was run over the #109 CMTI derivative-containing column with elution conditions as described above. Virtually all the material eluted immediately from the column (was not retained). In the test separation shown in FIGS. 3 and 4, a sample containing tPA added to human plasma standard was loaded onto the column and eluted as described above. As can be seen in FIGS. 3 and 4, the tPA was retained and the plasma proteins eluted in the void volume. Bound tPA was released at about 15.4 minutes. It was estimated that the tPA was released at about pH 4. The tPA peak was collected and examined using a silver-stained, reducing SDS-polyacrylamide gel, and, when compared with the starting material, was found to be >95% pure.

EXAMPLE 2

The tPA affinity ligands isolated from the CMTI library were examined further in order to design additional candidate domains that might bind to tPA as well.

As noted above, almost all of the variegation in amino acid positions used in building the CMTI library occurred between two cyteines at positions 3 and 10 of CMTI-I (see Table 3). In the parental CMTI protein, these cysteines form disulfide bonds with other cysteine residues elsewhere in the protein (see SEQ ID NO: 1), however with the successful isolation of affinity ligands from the CMTI library, a secondary library was conceptualized which was based on variegating a truncated 15-amino acid segment of the isolate #109 (see amino acids 1–15 of SEQ ID NO: 12). If the $C_3$ and $C_{10}$ cysteines of these members formed a disulfide bond, then a constrained loop having tPA binding properties might be obtained. Initial studies with the 15-amino acid segment derived from affinity ligand isolate #109 bound to a chromatographic support indicated that the $C_3$–$C_{10}$ loop formed and that the immobilized loop bound to tPA.

The foregoing experiments point to two new families of tPA affinity ligands isolated in accordance with this invention, comprising polypeptides including the sequences:

Arg-$X_1$-Cys-$X_2$-$X_3$-$X_4$-$X_5$-$X_6$-$X_7$-Cys-$X_8$Lys-Asp-Ser-Asp-Cys-Leu-Ala-Glu-Cys-Val-Cys-Leu-Glu-His-Gly-Tyr-Cys-Gly (SEQ ID NO:42) and Arg-$X_1$-Cys-$X_2$-$X_3$-$X_4$-$X_5$-$X_6$-$X_7$-Cys-$X_8$ (SEQ ID NO:43), wherein $X_1$ is Trp or Leu; $X_2$ is Pro, Ser, Thr or Ile; $X_3$ is Arg, Lys or Thr; $X_4$ is Ser, Tyr, Thr or Ala; $X_5$ is Ser, Tyr, Asp, Val, Pro, Ala, His, Asn or Thr; $X_6$ is Leu, Met, Gn, Arg or Lys; $X_7$ is Glu, Gly or Arg; and $X_8$ is at least Lys or Met. Since the presence of Met residues at position 11 in the sequence was not planned but turned out to be favored for binding to tPA, it is likely that other amino acids, for instance other non-polar amino acids such as Ala, Val, Leu, He, Phe, Pro or Trp substituted at position 11 will provide additional tPA-binding analogues.

Following the foregoing description, the characteristic important for the separation of tPA from any feed stream can be engineered into the binding domains of a designed library, so that the method of this invention invariably leads to several affinity ligand candidates suitable for separation of the tPA under desirable conditions of binding and release. High yield of the tPA without inactivation or disruption of the product, with high purity, with the elimination of even closedly related impurities, at acceptable cost and with re-usable or recyclable materials all can be achieved according to the present invention. Additional embodiments of the invention and alternative methods adapted to a particular tPA form or feed stream will be evident from studying the foregoing description. All such embodiments and alternatives are intended to be within the scope of this invention, as defined by the claims that follow.

REFERENCES

Boschetti, E., *J. Chromatography*, A 658: 207–236 (1994).

Ladner, R. C., "Constrained peptides as binding entities," *Trends in Biotechnology*, 13(10): 426–430 (1995).

Markland, W., Roberts, B. L., Ladner, R. C., "Selection for Protease Inhibitors Using Bacteriophage Display," *Methods in Enzymology*, 267: 28–51 (1996).

Narayanan, S. R., "Preparative affinity chromatography of proteins," *J. Chrom.* A, 658: 237–258 (1994).

Knight, P., *BioTechnology*, 8: 200 (1990).

Vedvick, T., Buckholtz, R. G., Engel, M., Urcam, M., Kinney, S., Provow, S., Siegel, R. S., and Thill, G. P., "High level secretion of biologically active aprotinin from the yeast *Pichia pastoris*", *J. Industrial Microbiol.*, 7: 197–202 (1991).

Wagner, S. L., Siegel, R. S., Vedvick, T. S., Raschke, W. C., and Van Nostrand, W. E., "High level expression, purification, and characterization of the Kunitz-type protease inhibitor domain of protease Nexin-2/amyloid β-protein precursor," *Biochem. Biphys. Res. Comm.*, 186: 1138–1145 (1992).

What is claimed is:

1. An isolated nucleic acid encoding an affinity ligand, said ligand comprising:

Arg-$X_1$-Cys-$X_2$ -$X_3$ -$X_4$ -$X_5$ -$X_6$ -$X_7$ -Cys-$X_8$ (SEQ ID NO:43), wherein $X_1$ is Trp or Leu;
$X_2$ is Pro, Ser, Thr or Ile;
$X_3$ is Arg, Lys or Thr;
$X_4$ is Ser, Tyr, Thr or Ala;
$X_5$ is Ser, Tyr, Asp, Val, Pro, Ala, His, Asn or Thr;
$X_6$ is Leu, Met, Gln, Arg or Lys;
$X_7$ is Glu, Gly or Arg; and
$X_8$ is Lys, Met, Ala, Val, Leu, Ile, Phe, Pro or Trp; and
wherein said affinity ligand binds tPA.

2. The isolated nucleic acid according to claim 1, wherein said nucleic acid encodes a ligand comprising an amino acid sequence selected from the group consisting of:

RWCPKTSLGCM (residues 1–11 of SEQ ID NO:4);
RLCPKTYLGCM (residues 1–11 of SEQ ID NO:5);
RWCSTYSLGCM (residues 1–11 of SEQ ID NO:6);
RLCPKTSLECM (residues 1–11 of SEQ ID NO:8);
RWCSKSSLECM (residues 1–11 of SEQ ID NO:11);
RLCPKTDLGCM (residues 1–11 of SEQ ID NO:12);
RWCPKSSMGCK (residues 1–11 of SEQ ID NO:13);
RWCPRTVQECM (residues 1–11 of SEQ ID NO:14);
RWCPTAPLECM (residues 1–11 of SEQ ID NO:15);
RWCPKSALDCK (residues 1–11 of SEQ ID NO:17);
RWCTKTSRECM (residues 1–11 of SEQ ID NO:18);
RWCIRTDLGCM (residues 1–11 of SEQ ID NO: 19);
RWCPRTVRRCM (residues 1–11 of SEQ ID NO:21);
RWCPKTHKECM (residues 1–11 of SEQ ID NO:22);
RWCPKTSLECM (residues 1–11 of SEQ ID NO:23);
RWCPKSTLGCM (residues 1–11 of SEQ IID NO:24);
RWCPKYTLECM (residues 1–11 of SEQ IID NO:26);
RWCPRSSLECM (residues 1–11 of SEQ ID NO:27);
RWCPRSNLECM (residues 1–11 of SEQ ID NO:29) and;
RWCPRSTLECM (residues 1–11 of SEQ ID NO:34).

3. The isolated nucleic acid according to claim 1, wherein said nucleic acid encodes a ligand comprising an amino acid sequence selected from the group consisting of:

RWCPKTSLGCMKDSDCLAECVCLEHGYCG(SEQ ID NO:4);

RLCPKTYLGCMKDSDCLAECVCLEHGYCG (SEQ ID NO:5);
RWCSTYSLGCMKDSDCLAECVCLEHGYCG (SEQ ID NO:6);
RLCPKTSLECMKDSDCLAECVCLEHGYCG (SEQ ID NO:8);
RWCSKSSLECMKDSDCLAECVCLEHGYCG (SEQ ID NO:11);
RLCPKTDLGCMKDSDCLAECVCLEHGYCG (SEQ ID NO:12);
RWCPKSSMGCKKDSDCLAECVCLEHGYCG (SEQ ID NO:13);
RWCPRTVQECMKDSDCLAECVCLEHGYCG (SEQ ID NO:14);
RWCPTAPLECMKDSDCLAECVCLEHGYCG (SEQ ID NO:15);
RWCPKSALDCKIKDSDCLAECVCLEHGYCG (SEQ ID NO:17);
RWCTKTSRECMKDSDCLAECVCLEHGYCG (SEQ ID NO:18);
RWCIRTDLGCMKDSDCLAECVCLEHGYCG (SEQ ID NO:19);
RWCPRTVRRCMKDSDCLAECVCLEHGYCG (SEQ ID NO:21);
RWCPKTHKEC MKDSDCLAECVCLEHGYCG (SEQ ID NO:22);
RWCPKTSLECMKDSDCLAECVCLEHGYCG (SEQ ID NO:23);
RWCPKSTLGCMKDSDCLAECVCLEHGYCG (SEQ ID NO:24);
RWCPKYTLECMKDSDCLAECVCLEHGYCG (SEQ ID NO:26);
RWCPRSSLECMKDSDCLAECVCLEHGYCG (SEQ ID NO:27);
RWCPRSNIECMKDSDCLAECVCLEHGYCG (SEQ ID NO:29); and
RWCPRSTLECMKDSDCLAECVCLEHGYCG (SEQ ID NO:34).

4. A recombinant expression vector comprising a nucleic acid according to any one of claims 1–3.

5. A recombinant host cell transformed with the expression vector according to claim 4.

6. A recombinant host cell according to claim 5, wherein said host cell is a *Pichia pastoris* cell.

7. A method of producing an affinity ligand that binds tPA, comprising the steps of:

(a) culturing a host cell according to claim 5 under conditions that promote expression of a tPA affinity ligand encoded by said expression vector; and (b) isolating said tPA affinity ligand from said host cell.

8. The nucleic acid of claim 1, wherein the ligand comprises Arg-$X_1$-Cys-$X_2$-$X_3$-$X_4$-$X_5$-$X_6$-$X_7$-Cys-$X_8$Lys-Asp-Ser-Asp-Cys-Leu-Ala-Glu-Cys-Val-Cys-Leu-Glu-His-Gly-Tyr-Cys-Gly, SEQ ID NO:42).

9. The nucleic acid of claim 1, wherein $X_8$ is Lys or Met.

10. The nucleic acid of claim 1, wherein $X_1$ is Trp.

11. The nucleic acid of claim 1, wherein $X_1$ is Leu.

12. The nucleic acid of claim 1, wherein $X_3$ is Arg.

13. The nucleic acid of claim 1, wherein $X_3$ is Lys.

14. The nucleic acid of claim 1, wherein $X_3$ is Thr.

15. The nucleic acid of claim 1, wherein $X_7$ is Glu.

16. The nucleic acid of claim 1, wherein $X_7$ is Gly.

17. The nucleic acid of claim 1, wherein $X_7$ is Arg.

18. The nucleic acid of claim 1, wherein said affinity ligand binds tPA at pH 7.0.

19. The nucleic acid of claim 2, wherein the ligand comprises RLCPKTDLGCM (residues 1–11 of SEQ ID NO:12).

20. The nucleic acid of claim 1, wherein the ligand comprises RLCPKTYLGCM (residues 1–11 of SEQ ID NO:5).

21. The nucleic acid of claim 1, wherein the ligand comprises RLCPKTSLECM (residues 1–11 of SEQ ID NO:8).

22. The nucleic acid of claim 1, wherein the ligand comprises RWCSKSSLECM (residues 1–11 of SEQ ID NO:11) or RWCSTYSLGCM (residues 1–11 of SEQ ID NO:6).

23. A recombinant expression vector comprising a nucleic acid according to any one of claims 8–22.

24. A recombinant host cell transformed with the expression vector according to claim 23.

25. A method of producing an affinity ligand that binds tPA, comprising the steps of:

(a) culturing a host cell according to claim 24 under conditions that promote expression of a tPA affinity ligand encoded by said expression vector; and (b) isolating said tPA affinity ligand from said host cell.

* * * * *

UNITED STATES PATENT AND TRADEMARK OFFICE
CERTIFICATE OF CORRECTION

| | | |
|---|---|---|
| PATENT NO. | : 7,074,560 B2 | Page 1 of 1 |
| APPLICATION NO. | : 10/193588 | |
| DATED | : July 11, 2006 | |
| INVENTOR(S) | : Maclenna et al. | |

It is certified that error appears in the above-identified patent and that said Letters Patent is hereby corrected as shown below:

Column 39, claim 3, line 17 "RWPCKSALDCKIKDSDCLAECVCLEHGYCG" delete " I "

Column 40, claim 8, line 6 "$X_8Lys$" should be -- $X_8$-Lys--

Signed and Sealed this

Thirty-first Day of July, 2007

JON W. DUDAS
*Director of the United States Patent and Trademark Office*